United States Patent
Sellars

(10) Patent No.: US 10,546,654 B2
(45) Date of Patent: Jan. 28, 2020

(54) METHOD AND SYSTEM FOR INTELLIGENT COMPLETION OF MEDICAL RECORD BASED ON BIG DATA ANALYTICS

(71) Applicant: DrFirst.com, Inc., Rockville, MD (US)

(72) Inventor: David Andrew Sellars, Zanesfield, OH (US)

(73) Assignee: DrFirst.com, Inc., Rockville, MD (US)

( * ) Notice: Subject to any disclaimer, the term of this patent is extended or adjusted under 35 U.S.C. 154(b) by 405 days.

(21) Appl. No.: 14/972,209

(22) Filed: Dec. 17, 2015

(65) Prior Publication Data

US 2017/0177796 A1 Jun. 22, 2017

(51) Int. Cl.
*G06F 19/00* (2018.01)
*G16H 10/60* (2018.01)

(52) U.S. Cl.
CPC .......... *G16H 10/60* (2018.01); *G06F 19/00* (2013.01)

(58) Field of Classification Search
CPC ........ G06F 19/322; G06F 19/00; G16H 10/60
USPC ......................................................... 705/2–3
See application file for complete search history.

(56) References Cited

U.S. PATENT DOCUMENTS

| | | | |
|---|---|---|---|
| 5,544,044 A * | 8/1996 | Leatherman | G06F 19/324 705/3 |
| 6,024,699 A * | 2/2000 | Surwit | G06F 19/3418 600/300 |
| 6,697,783 B1 | 2/2004 | Brinkman et al. | |
| 6,915,254 B1 * | 7/2005 | Heinze | G06F 17/27 704/9 |
| 7,664,660 B2 * | 2/2010 | Korpman | G06F 19/322 705/2 |
| 7,860,925 B1 | 12/2010 | Gheorghe et al. | |
| 8,239,213 B1 | 8/2012 | Paul et al. | |
| 8,473,310 B2 * | 6/2013 | Hasan | G06F 19/322 705/2 |
| 8,694,300 B2 * | 4/2014 | Morris | G16H 50/30 703/11 |

(Continued)

FOREIGN PATENT DOCUMENTS

WO 02/095650 A2 11/2002

OTHER PUBLICATIONS

Haug, James D. "Physicians' preferences for information sources: a meta-analytic study." Bulletin of the Medical Library Association 85.3 (1997): 223.*

(Continued)

*Primary Examiner* — Mark Holcomb
(74) *Attorney, Agent, or Firm* — Brake Hughes Bellermann LLP

(57) ABSTRACT

The present teaching relates to medical record completion. In one example, a medical record of a patient is received. The medical record is associated with a plurality of components comprising a first component with a populated value and a second component with an unpopulated value. The unpopulated value of the second component is estimated based on the populated value of the first component in accordance with a first model. Information associated with the medical record and/or the patient is obtained. The values of the first and second components are validated based on the obtained information in accordance with a second model. The first and second models are dynamically updated based on data related to medical transactions of a plurality of patients.

21 Claims, 18 Drawing Sheets

(56) References Cited

U.S. PATENT DOCUMENTS

| | | |
|---|---|---|
| 10,192,639 B2 | 1/2019 | Sellars |
| 2003/0046114 A1 | 3/2003 | Davies et al. |
| 2003/0125985 A1* | 7/2003 | Rao .................. G06F 16/30 |
| | | 705/2 |
| 2006/0025657 A1 | 2/2006 | Rosenfeld et al. |
| 2006/0218012 A1* | 9/2006 | Hernandez ............. G16H 10/60 |
| | | 705/3 |
| 2006/0275844 A1 | 12/2006 | Linke et al. |
| 2006/0278241 A1 | 12/2006 | Ruano |
| 2008/0133275 A1 | 6/2008 | Huag |
| 2008/0162352 A1 | 7/2008 | Gizewski |
| 2011/0105852 A1 | 5/2011 | Morris et al. |
| 2011/0246240 A1* | 10/2011 | Hasan .................. G06F 19/322 |
| | | 705/3 |
| 2012/0041789 A1 | 2/2012 | Sweeney |
| 2012/0078837 A1* | 3/2012 | Bagchi ................... A61B 5/00 |
| | | 706/52 |
| 2012/0179481 A1 | 7/2012 | Patel |
| 2014/0046889 A1 | 2/2014 | Biem et al. |
| 2014/0136226 A1 | 5/2014 | Dittmer et al. |
| 2015/0066539 A1* | 3/2015 | Sheffer .................. G06Q 50/22 |
| | | 705/3 |
| 2015/0073828 A1 | 3/2015 | Mortara et al. |
| 2015/0081321 A1 | 3/2015 | Jain |
| 2015/0294069 A1* | 10/2015 | Shah ..................... G06F 19/322 |
| | | 705/3 |
| 2016/0019346 A1* | 1/2016 | Boston .................. G16H 10/60 |
| | | 705/3 |
| 2016/0350486 A1* | 12/2016 | Plunkett ............... G06Q 50/24 |
| 2017/0177796 A1* | 6/2017 | Sellars ................... G06F 19/00 |

OTHER PUBLICATIONS

Office Action dated Dec. 30, 2016 in U.S. Appl. No. 14/466,663.
International Search Report and Written Opinion dated Apr. 8, 2016 in PCT/US2016/016128.

* cited by examiner

| Drug ID | Action | Dose | Unit | Route | Timing | Duration | Dispense | Dispense Quantity | Related Disease | Refill |
|---------|--------|------|------|-------|--------|----------|----------|-------------------|-----------------|--------|

Dimension – Specialty

| | Cardiology | Neurosurgery | Psychiatry |
|---|---|---|---|
| Medical Suggestion 1 | Score | Score | Score |
| Medical Suggestion 2 | Score | Score | Score |
| Medical Suggestion 3 | Score | Score | Score |
| Medical Suggestion 4 | Score | Score | Score |
| Medical Suggestion 5 | Score | Score | Score |
| Medical Suggestion 6 | Score | Score | Score |
| Medical Suggestion 7 | Score | Score | Score |

FIG. 16

METHOD AND SYSTEM FOR INTELLIGENT COMPLETION OF MEDICAL RECORD BASED ON BIG DATA ANALYTICS

BACKGROUND

1. Technical Field

The present teaching relates to methods, systems and programming for health care. More specifically, the present teaching relates to methods, systems, and programming for medical record completion.

2. Discussion of Technical Background

In health care information technology, existing systems allow for a prescriber, e.g., a doctor who writes a medication prescription, to make a request for medication history from various sources and to make sure there are no drug-drug or drug-allergy interactions. Existing systems also allow for individuals working at a hospital or other institution to request medication history in order to conduct medication reconciliation when a patient being admitted to a hospital, to make sure the hospital knows of what the patient is taking upon admission, to evaluate disease, diagnosis, and to ensure there are no drug-drug or drug-allergy interactions.

However, existing systems do not always provide all of the information comprising of medical records and do not always provide the medical record information in accordance with the receiving system's desired format. Thus, people may waste time to conduct manual data entry or not have a clear understanding of the appropriate systems.

Therefore, there is a need to provide a solution for medical record completion to avoid the above-mentioned drawbacks.

SUMMARY

The present teaching relates to methods, systems and programming for health care. More specifically, the present teaching relates to methods, systems, and programming for medical record completion.

In one example, a method, implemented on at least one computing device each of which has at least one processor, storage, and a communication platform connected to a network for completing a medical record is presented. A medical record of a patient is received. The medical record is associated with a plurality of components comprising a first component with a populated value and a second component with an unpopulated value. The unpopulated value of the second component is estimated based on the populated value of the first component in accordance with a first model. Information associated with the medical record and/or the patient is obtained. The values of the first and second components are validated based on the obtained information in accordance with a second model. The first and second models are dynamically updated based on data related to medical transactions of a plurality of patients.

In a different example, a system for completing a medical record is presented. The system includes a missing component completing module and a medical record validating module. The missing component completing module is configured for receiving a medical record of a patient. The medical record is associated with a plurality of components comprising a first component with a populated value and a second component with an unpopulated value. The missing component completing module is further configured for estimating the unpopulated value of the second component based on the populated value of the first component in accordance with a first model. The medical record validating module is configured for obtaining information associated with the medical record and/or the patient, and validating the values of the first and second components based on the obtained information in accordance with a second model. The first and second models are dynamically updated based on data related to medical transactions of a plurality of patients.

Other concepts relate to software for implementing the present teaching on medical record completion. A software product, in accord with this concept, includes at least one non-transitory, machine-readable medium and information carried by the medium. The information carried by the medium may be executable program code data, parameters in association with the executable program code, and/or information related to a user, a request, content, or information related to a social group, etc.

In one example, a non-transitory, machine-readable medium having information recorded thereon for completing a medical record is presented. A medical record of a patient is received. The medical record is associated with a plurality of components comprising a first component with a populated value and a second component with an unpopulated value. The unpopulated value of the second component is estimated based on the populated value of the first component in accordance with a first model. Information associated with the medical record and/or the patient is obtained. The values of the first and second components are validated based on the obtained information in accordance with a second model. The first and second models are dynamically updated based on data related to medical transactions of a plurality of patients.

BRIEF DESCRIPTION OF THE DRAWINGS

The methods, systems and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 14 illustrates exemplary components of a normalized medical record, according to an embodiment of the present teaching;

FIG. 16 illustrates an exemplary medical suggestion data map in one analytic influence dimension in a medical suggestion database, according to an embodiment of the present teaching;

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The present teaching describes methods, systems, and programming aspects of intelligent medical record completion based on big data analytics. The users may include personnel in hospitals, clinics, and/or other health care facilities that are authorized to prescribe medication drugs, make other medical suggestions (e.g., physical therapies, diets, lab tests, radiology tests, etc.) to patients, or perform medication reconciliation. The method and system in the present teaching may evaluate missing information in a received medical record against a repository of historical medication strings in order to determine the missing information from the specific medical record. The method and system in the present teaching may also validate information of a received medical record against a repository of historical medication suggestions in order to identify any possible errors in the received medical record under the current patient care setting. Moreover, the method and system in the present teaching may tailor the resulting medical record information to fit individual user's requirements, to relieve the issues of manual entry or duplicate entry, allowing for seamless integration with the existing health care systems.

Additional novel features will be set forth in part in the description which follows, and in part will become apparent to those skilled in the art upon examination of the following and the accompanying drawings or may be learned by production or operation of the examples. The novel features of the present teaching may be realized and attained by practice or use of various aspects of the methodologies, instrumentalities and combinations set forth in the detailed examples discussed below.

Figure 1:
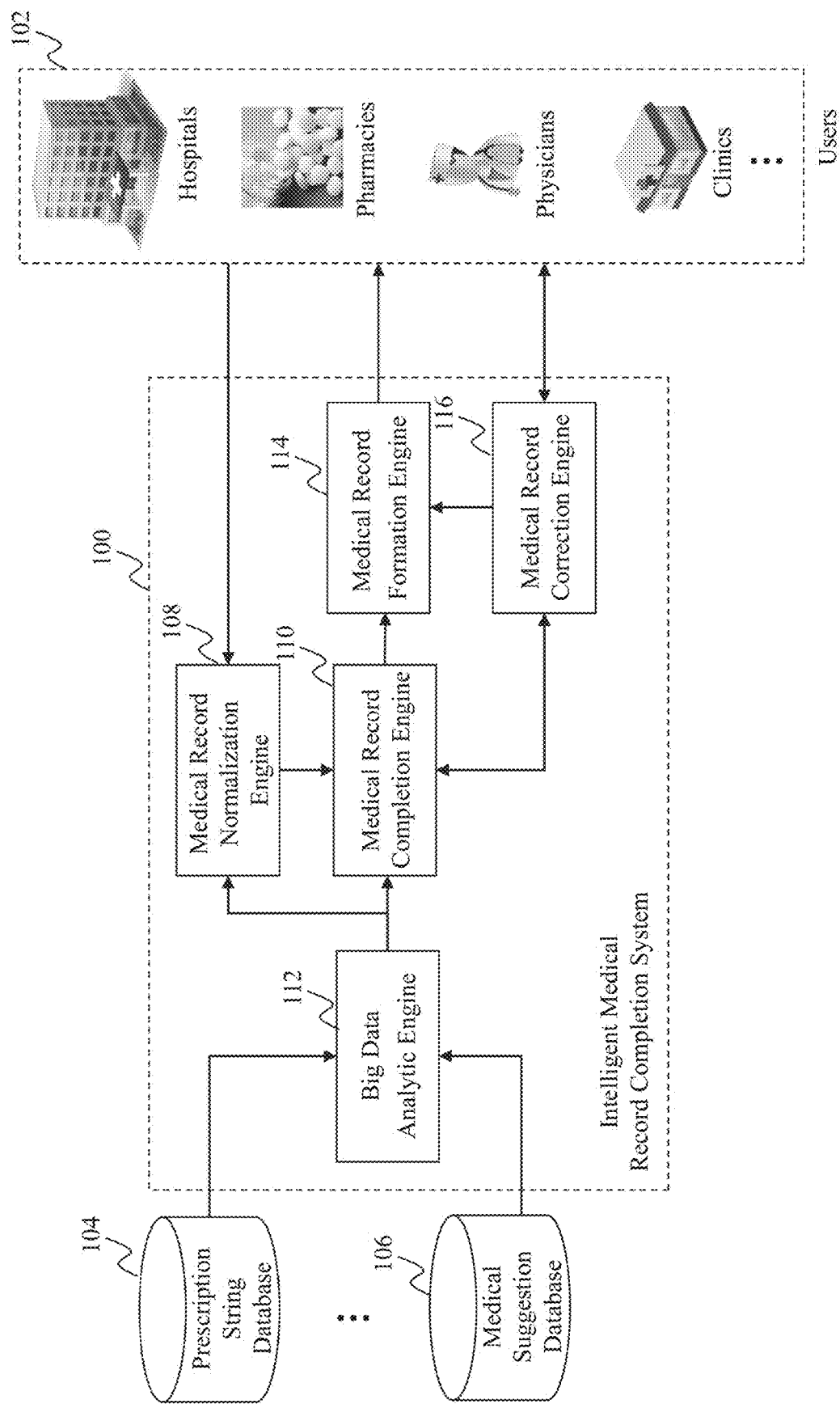
FIG. 1 illustrates an exemplary diagram of an intelligent medical record completion system, according to an embodiment of the present teaching.

FIG. 1 illustrates an exemplary diagram of an intelligent medical record completion system 100, according to an embodiment of the present teaching. The medical record completion system 100 in this embodiment serves as a medical record network exchange for transmitting medical records among different users 102. Users 102 may be of different types such as users connected to the medical record completion system 100 via a network from hospitals, pharmacies, clinics, individual physicians, insurance companies, etc. In one embodiment, a user 102 requests medical history of a patient from the medical record completion system 100. The medical record completion system 100 then collects medical records of the patient from other users 102. It is understood that the in other embodiments, the medical record may not be part of a patient's medical history. Instead, a user 102 may send a medical order including one or more medical records to another user 102 via the medical record completion system 100. The medical record may include, for example, a medication prescription including signetur (sig) and non-drug orders such as physical therapies, diets, lab tests, radiology tests, etc. For each received medical record (either as part of a patient's medical history or a medical order), the medical record completion system 100 can complete it by performing various processes including normalization, missing value completion, validation, and format conversion. The processes may be backed up by big data analytics based on, for example a prescription string database 104, a medical suggestion database 106, and other database mined from historical, actual medical transaction data of a general population of patients. The completed medical records are then sent by the medical record completion system 100 to the other user 102 who requests the patient's medical history or expects to receive the medical order in a format suitable for the user 102.

Any user 102 of the medical record completion system 100 can perform bi-directional communication with the medical record completion system 100 via the network. Via the network, a user 102 may send original (uncompleted) medical records in natural languages to the medical record completion system 100 when the medical record completion system 100 collects medical records from the users 102 and may also receive new (completed) medical records in a format suitable for this user 102 from the medical record completion system 100 when the user 102 requests medical history of a patient. In some embodiments, a user 102 may send a medical order to another user 102 via the medical record completion system 100, which normalizes, completes, and converts the original (uncompleted) medical record(s) in natural language(s) in the medical order to new (completed) medical record(s) in a format suitable for the other user 102 to receive the medical order. The network may be a single network or a combination of different networks. For example, the network may be a local area network (LAN), a wide area network (WAN), a public network, a private network, a proprietary network, a Public Telephone Switched Network (PSTN), the Internet, a wireless network, a virtual network, or any combination thereof. The network may also include various network access points, e.g., wired or wireless access points such as base stations or Internet exchange points, through which a data source may connect to the network in order to transmit information via the network.

In this embodiment, the medical record completion system 100 includes a medical record normalization engine 108, a medical record completion engine 110, a big data analytic engine 112, a medical record formation engine 114, and a medical record correction engine 116. Oftentimes, a medical record of a patient is in a natural language (e.g., a free text sig) with uncodified and non-uniform terms. For example, a physician may describe multiple components of a prescription including the dose, dose unit, route of administration, duration, dispense quantity, dispense quantity units, and refills all in one free text field, which may not be recognized and interpreted by computing devices directly. Additionally, different terms and ways of expression in a free text medical record may have the same meaning. For example, "oral," "by mouth," and "P.O." all have the same meaning for route of administration; and "taking twice a day," "taking two times daily," and "take every morning and night" all map to the same frequency. The medical record normalization engine 108 in this embodiment handles the different permutations in the received natural language medical records and normalizes them according to templates with standard components.

A predetermined template with standard components may be used for each type of medical record in normalization. Referring now to FIG. 14, a medication prescription template 1400 includes standard components of drug ID, action, dose, unit, route, timing, duration, dispense, dispense quantity, related disease, refill, etc. Each component may be associated with possible codified and uniform values. For example, the "drug ID" component may have values of national drug code (NDC), drug identification number (DIN), Med ID, or any other standard drug identifiers. For "route" component, the codified values may be standard terms such as "oral," "nasal," "intra-arterial" "intra-muscular," "transdermal," etc. Based on mining a large number of historical data of actual medical transactions (e.g., actual medication prescriptions), tables of permutations may be generated to map different permutations to one codified and uniform value. The tables may be dynamically updated in response to the new incoming medical transaction data.

Returning to FIG. 1, the medical record normalization engine 108 normalizes the received medical record to generate a normalized medical record having a plurality of components. The components may be determined based on a template having standard components for the type of medical record, such as the template 1400 used for medication prescriptions. In other examples, for non-drug medical records, a different template with other standard components may be used in normalization. The medical record normalization engine 108 then populates values for each component based on a model including one or more tables. Different permutations in the natural language medical records may be mapped to a codified and uniform value according to the tables generated by the big data analytic engine 112. In some cases, not all components have corresponding values populated from the natural language medical record by the medical record normalization engine 108. In other words, the components of a normalized medical record may include at least one component with populated values (known information) and at least one component with unpopulated values (missing information). The populated values may be predefined codified and uniform values that can be recognized and interpreted by the medical record completion system 100. In some embodiments, a standard value (e.g., null) may be temporarily used to represent the unpopulated value by the medical record completion system 100 until an estimated value is generated to replace it.

In this embodiment, the medical record completion engine 110 completes each normalized medical record by estimating the unpopulated values (if any) and validating the values (both populated values and estimated unpopulated values) of the components of the normalized medical record based on models provided by the big data analytic engine 112. If there is any missing information in the normalized medical record, the medical record completion engine 110 may estimate the unpopulated value of the component based on the populated values (known information) in accordance with a first model. The first model may include a plurality of medical records, each of which is associated with rankings with respect to each component. The ranked medical records may be mined from historical, actual medical transaction data of the general population of patients and may be dynamically updated upon receiving new medical transaction data.

When the medical record is a medication prescription, the prescription string database 104 may be used by the big data analytic engine 112 to provide the first model for estimating the missing values in the normalized medication prescription. Details of generating the prescription string database 104 are provided, for example, in U.S. patent application Ser. No. 14/466,663, filed Aug. 22, 2014, entitled "Method and System for Recommending Prescription Strings," which is incorporated herein by reference in its entirety.

Figure 15:
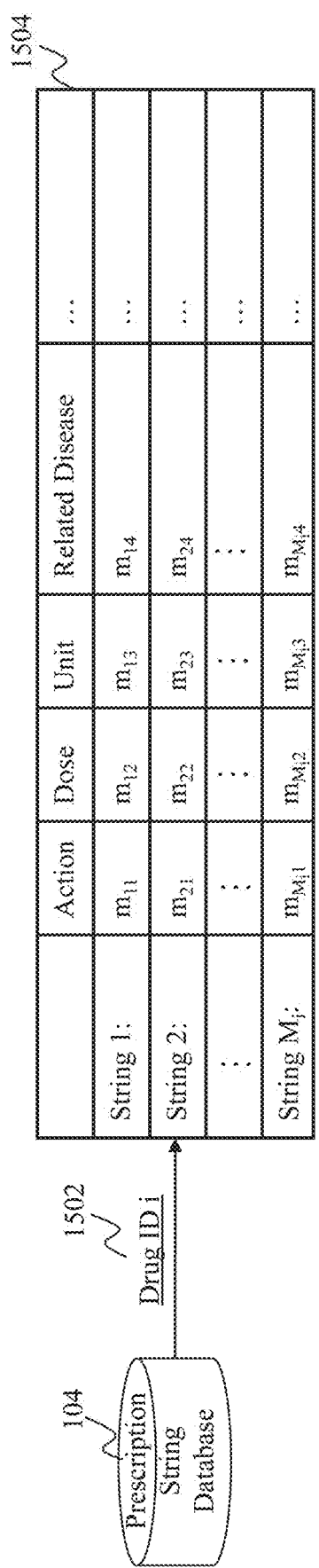
FIG. 15 illustrates exemplary medical records in a prescription string database, according to an embodiment of the present teaching.

Turning now to FIG. 15, an exemplary prescription string database 104 is disclosed. Historical, actual medical transaction data, e.g., data related to medication drugs from different sources including but not limited to pharmaceutical companies, researchers, and Food and Drug Administration (FDA) is collected. Candidate prescription strings are identified from the collected data and are automatically processed, e.g., based on statistical analytics, to generate a subset of prescription strings that are considered to be useful for future use. Each of the prescription strings in the subset is associated with a ranking with respect to each component of the string. The subset of prescription strings is stored in the prescription string database 104 and can be retrieved based on their rankings with respect to values of one or more components. The prescription strings in the prescription string database 104 may be retrieved by different components. As shown in FIG. 15, the prescription strings in the prescription string database 104 are retrieved by the drug ID. For example, based on drug ID i 1502, 1-$M_i$ prescription strings 1504 having the drug ID i 1502 are retrieved in a ranked order. Each of the 1-$M_i$ prescription strings 1504 may include standard components as mentioned before.

Returning back to FIG. 1, for example, based on at least one of the populated values of other components of the normalized medication prescription and the first model, any unpopulated value of a component of the normalized medication prescription may be estimated with a confidence score. For example, if the frequency is unknown in the received medication prescription, while the drug ID, unit, and duration are known (e.g., Tylenol tablet, 50 mg, 30 days, respectively), then the medical record completion engine 110 in conjunction with the big data analytic engine 112 can retrieve the top ranked prescription strings from the prescription string database 104 based on the known values (Tylenol tablet, 50 mg, 30 days) of the drug ID, unit, and duration components. From the retrieved top ranked prescription strings, the unpopulated value may be estimated with a confidence score based on the values of the corresponding component. For example, if the top two retrieved prescription strings are "Tylenol 50 mg tablet three times per day for 30 days (90% confidence score)," and "Tylenol 50 mg tablet once per day for 30 days (15% confidence score)," then the estimated value of frequency in the current medication prescription is "three times day (90% confidence score)" or "once per day (15% confidence score)."

As will be described later in detail, in some embodiments, the first model may be an inference model, and the unpopulated value of a component may be estimated based on one or more populated values of other components in the same medical record without looking into the prescription string database 104. In one example, a certain unpopulated value may be calculated directly based on one or more populated values. For example, if the populated values include "taking a tablet three times a day for 10 days" and the dispense quantity is known as "30 tablets," then the dose can be calculated directly as "one tablet" by a mathematical equation. In another example, a certain unpopulated value may be estimated based on patient's information and/or common medical knowledge. For example, for a Tylenol tablet, even the natural language medical record does not specify the route of administration, i.e., the value of route component is unpopulated, based on common medical knowledge, the value is most likely "oral".

On the other hand, the medical record completion engine 110 may also validate the values of the normalized medical record. The purpose of validation is to see whether all values in the normalized medical record make clinical sense in view of known information mined from historical, actual medical transaction data of the general population of patients. In this embodiment, a second model provided by the big data analytic engine 112 based on the medical suggestion database 106 may be used by the medical record completion engine 110 in validation. Details of generating the medical suggestion database 106 are provided, for example, in U.S. patent application Ser. No. 14/613,174, filed Feb. 3, 2015, entitled "Method and System for Medical Suggestion Search," which is incorporated herein by reference in its entirety.

Similar to the prescription string database 104, historical, actual medical transaction data, e.g., data related to medication drugs from different sources, is collected to build and update the medical suggestion database 106. Candidate medical suggestions (medication prescriptions and non-drug medical records) are identified from the collected data and are automatically processed, e.g., based on statistical analytics, to generate confidence scores for each candidate medical suggestion. The candidate medical suggestions and their confidence scores are then processed and stored with respect to each analytic influence dimension, e.g., doctor specialty, patient profile, disease diagnosis, and symptoms. Based on the patient care setting, e.g., analytic influence information in one or more dimensions received with medical record, the medical record completion engine 110 in conjunction with the big data analytic engine 112 can apply a mathematical approach to determine qualified medical suggestions that are suitable for the particular patient care setting. Those retrieved medical suggestions are considered as being clinically proven under the particular patient care setting and thus, can be used to validate the corresponding values of a medical record in the same or similar patient care setting.

Turning now to FIG. 16, an exemplary medical suggestion data map in one dimension is illustrated. In this example, qualified medical suggestions with their confidence scores may be stored in the medical suggestion database 106 in the form of nomenclature dimension maps. Each nomenclature dimension map may include one or more types of medical suggestions with their confidence scores with respect to a particular analytic influence dimension. In this example, the map includes qualified medical suggestions with their confidence scores with respect to the "doctor specialty" dimension. Each of the qualified medical suggestions (medical suggestion 1, medical suggestion 2, . . . ) has a confidence score with respect to each doctor specialty (Cardiology, Neurosurgery, . . . ). For example, the confidence score of medical suggestion 1 with respect to Cardiology indicates a degree of match between medical suggestion 1 and Cardiology. In one example, such confidence score may be the number of total occurrences that cardiologists have prescribed medical suggestion 1 mined from historical medical transaction data. Similarly, other nomenclature dimension maps may include qualified medical suggestions with their confidence scores with respect to other dimensions, e.g., patient age, gender, disease diagnosis, etc. The nomenclature dimension maps may also be organized based on the types of medical suggestions (e.g., medication prescription and non-drug medical records). That is, different types of medical suggestions may be arranged in different dimension maps. In other embodiments, multiple types of medical suggestions may be mixed up in the same dimension map.

Back to FIG. 1, in order to validate the normalized medical record against qualified medical suggestions in the same or similar patient care setting, the medical record completion engine 110 also obtains analytic influence information associated with the received medical record and/or the patient. Based on the received analytic influence information in multiple dimensions, the patient care setting associated with the received medical record is determined and used to retrieve the relevant qualified medical suggestions, which are in turn used for comparing with the values of the received medical record for validation purpose. A confidence score may be calculated for the validation process and indicates the level of matching between the values in the received medical record and the corresponding values in the qualified medical suggestions. A flag may be raised if the confidence score falls under a threshold, which indicates that one or more values of the received medical record may not make clinical sense.

In this embodiment, the medical record correction engine 116 may notify a user 102 from whom the medical record is received about the invalid value in the medical record. Optionally, one or more suggested values based on the qualified medical suggestions may be provided as well for the user 102's reference. If the user 102 in response to the notification, provides an updated medical record with a corrected value, then the medical record correction engine 116 may cause the medical record completion engine 110 to re-validate the updated medical record.

In this embodiment, the medical record formation engine 114 is configured to generate a completed medical record based on the validated values (both the populated values and the estimated unpopulated values) in a format that is suitable for another user 102 to receive the completed medical record. In one example, the format may be explicitly provided by the user 102 receiving the completed medical record. In another example, if the format is not explicitly provided, the medical record formation engine 114 may analyze the past medical records sent by the user 102 to the medical record completion system 100 to determine the format that the user 102 prefers using.

Figure 2:
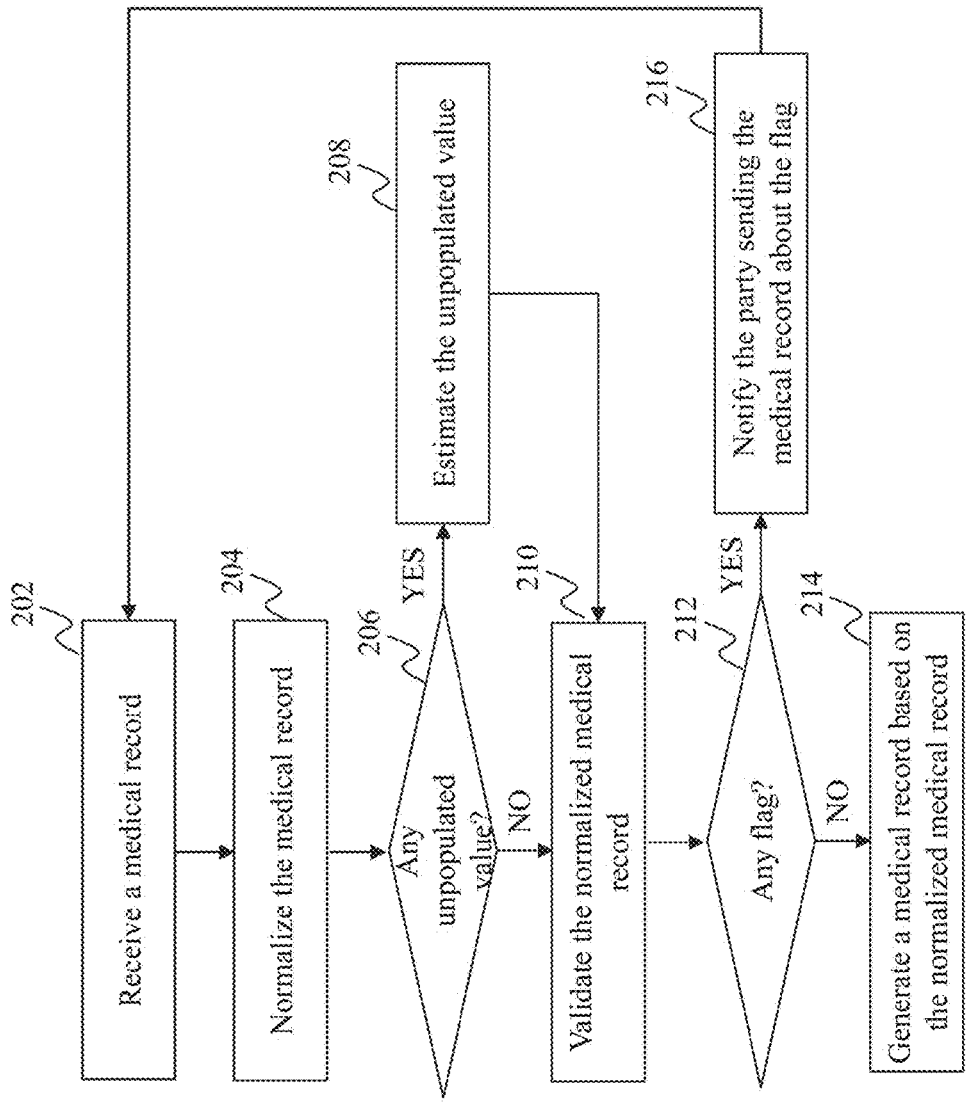
FIG. 2 is a flowchart of an exemplary process performed by the intelligent medical record completion system, according to an embodiment of the present teaching.

FIG. 2 is a flowchart of an exemplary process performed by the intelligent medical record completion system 100, according to an embodiment of the present teaching. Starting at 202, a medical record of a patient is received. The medical record may include, for example, a medication prescription including sig and non-drug orders such as physical therapies, diets, lab tests, radiology procedures, etc. In this embodiment, the medical record is in a natural language, i.e., a free text medical record. The medical record may be received from hospitals, clinics, individual physicians, pharmacies, and insurance companies. At 204, the medical record is normalized. For example, for a free text medical record, the text may be parsed to populate values of standard components of a particular type of medical record, e.g., a sig. Different term permutations may be mapped to the same codified value of a standard component. A normalized medical record thus may include a plurality of components. For example, for a normalized medication prescription, it includes components such as drug ID, action, dose, unit, route, timing, duration, frequency, dispense, dispense quantity, etc. At 206, whether any component has an unpopulated value is determined. If at least one component has an unpopulated value, then the unpopulated value is estimated at 208. The unpopulated value may be estimated based on one or more populated values of other components in accordance with a first model. The first model may include a plurality of medical records that are dynamically updated based on data related to medical transactions of a plurality of patients. Each medical record in the first model may be associated with rankings with respect to the components.

At 210, the normalized medical record is validated. For example, all the populated values and estimated unpopulated values of the components may be validated based on information associated with the received medical record and/or the patient in accordance with a second model. The information may be analytic influence information in various dimensions including the doctor specialties, disease diagnosis, symptoms, and patient profile (e.g., age, gender, age, race, etc.). The second model may include a plurality of medical records (medical suggestions) that are dynamically updated based on data related to medical transactions of a plurality of patients. Each medical suggestion in the second model may be associated with rankings with respect to the analytic influence dimensions. If a component of the normalized medical record fails the validation process at 210, a flag may be raised. At 212, whether the normalized medical record is associated with any flag is checked. If a flag is raised, at 216 the party from whom the medical record is received is notified. Optionally, a suggested value may be provided as well. The process may be returned to 202 if the sending party resends an updated medical record after receiving the notification. If no flag is detected at 212, in other words, the normalized medical record is successfully validated, then at 214, a medical record is generated based on the normalized medical record. For example, the generated new medical record is a completed medical record including estimated unpopulated values that have been validated. The generated new medical record may also be converted to a format that is suitable for another user to whom the medical record is sent.

Figure 3:
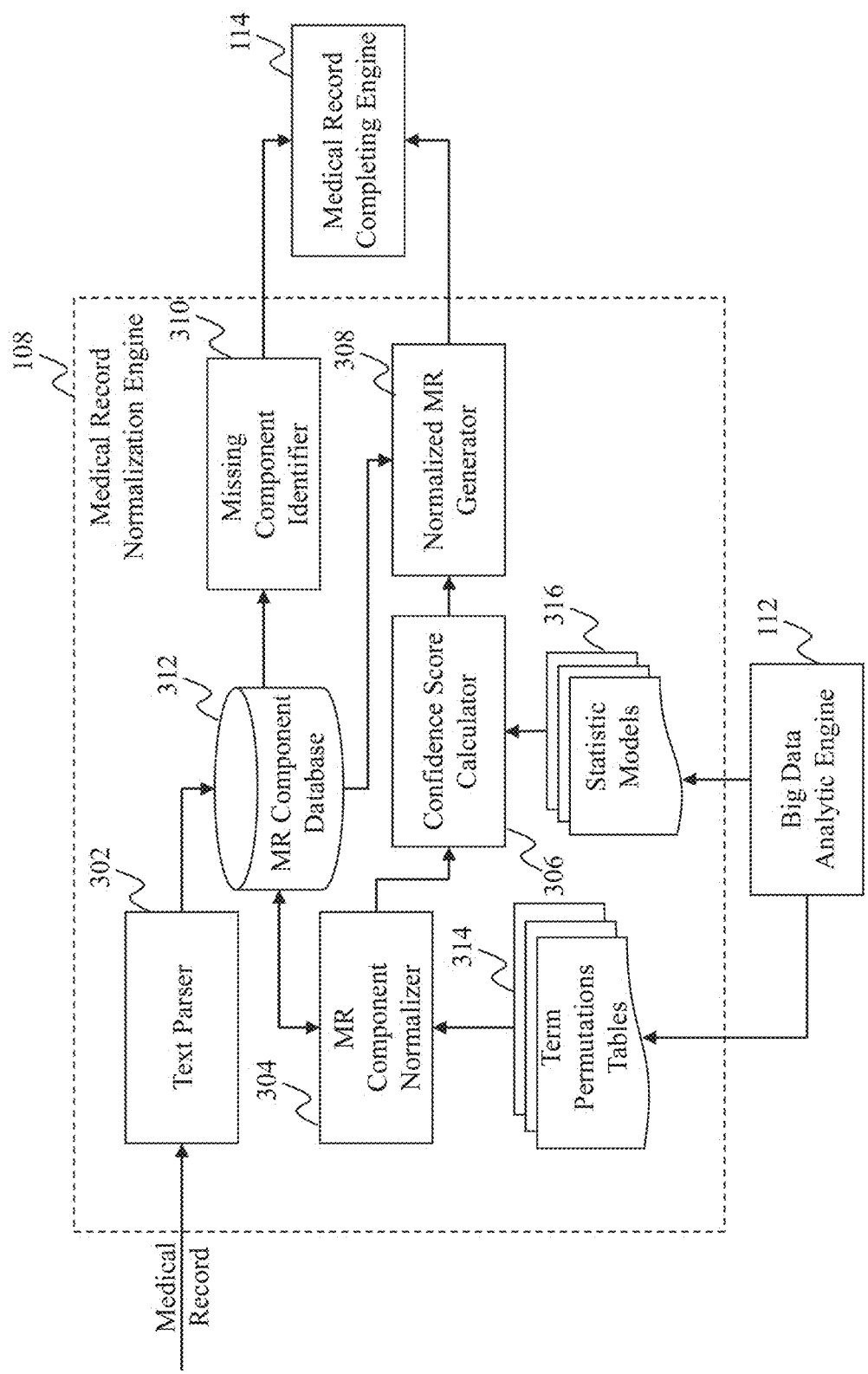
FIG. 3 illustrates an exemplary diagram of a medical record normalization engine, according to an embodiment of the present teaching.

FIG. 3 illustrates an exemplary diagram of a medical record normalization engine 108, according to an embodiment of the present teaching. The medical record normalization engine 108 in this embodiment includes a text parser 302, a medical record (MR) component normalizer 304, a confidence score calculator 306, a normalized MR generator 308, and a missing component identifier 310. The text parser 302 parses the text of the medical record in a natural language into components, for example, based on a template of standard components for the type of medical record. The parsed text for each component may be stored in the MR component database 312. The MR component normalizer 304 is configured to normalize each component to populate codified and uniform values. Any known semantic analysis approach may be applied by the MR component normalizer 304 to understand the meaning of the parsed text for each component. Term permutations tables 314 are provided by the big data analytic engine 112 to provide mapping from various term permutations to the same codified and uniform value. The term permutations tables 314 are generated based on historical, actual medical transaction data and are dynamically updated as new medical transaction data comes in. In other words, the MR component normalizer 304 populates standard values for each component of the medical record, which may be updated and stored in the MR component database 312 to replace the previously stored uncodified and non-uniform values (e.g., text) of each component.

As the term permutations tables 314 may be generated based on statistic models 316 by the big data analytic engine 112, the confidence score calculator 306 may calculate a confidence score for the normalization process based on the statistic models 316. For example, when mapping the terms "taken by mouth" and "P.O." to the standard value "oral" for the "route" component, the confidence score may be very high, e.g., 99%, as those terms frequently appeared in the historical medical transaction data. For some rarely-appeared term permutations, the confidence score may be relatively low when they are normalized. It is understood that human manual intervention may be applied for adjusting the term permutations tables 314 based on common knowledge. The normalized MR generator 308 then generates the normalized medical record based on the populated values stored in the MR component database 312 and associates it with the confidence score calculated by the confidence score calculator 306.

As mentioned before, certain information may be missing from the original medical record either by mistake or for simplicity. The missing component identifier 310 may check the values stored in the MR component database 312 to see if all the components of the medical record have corresponding values populated. If any value is not populated, the corresponding component is labeled as a "missing component" with an unpopulated value (e.g., null). The normalized medical record and the missing component information (if any) are provided to the medical record completion engine 110.

Figure 4:
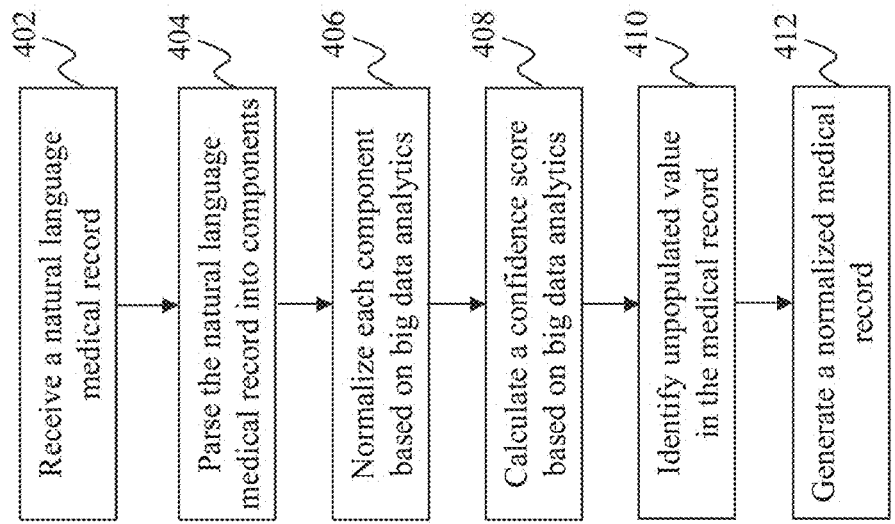
FIG. 4 is a flowchart of an exemplary process performed by the medical record normalization engine, according to an embodiment of the present teaching.

FIG. 4 is a flowchart of an exemplary process performed by the medical record normalization engine 108, according to an embodiment of the present teaching. Starting at 402, a medical record of a patient in a natural language (e.g., a free text sig) is received. At 404, the natural language medical record is parsed into components. Based on the specific type of medical record, a template with standard components for this type of medical record may be used for parsing. At 406, values of each component may be normalized based on big data analytics. For example, term permutations tables generated based on mining of historical, actual medical transaction data may be used to populate codified and uniform values. As the normalization process may be based on a statistic model, at 408, a confidence score may be calculated for the normalization process based on big data analytics of the statistic model. At 410, any unpopulated value of a component in the medical record is identified. In other words, any missing information in the received natural language medical record is detected. At 412, a normalized medical record is generated. The normalized medical record may be associated with a confidence score and include a plurality of components. Each component has either a codified value populated in the normalization process or has an unpopulated value missing from the original medical record.

Figure 5:
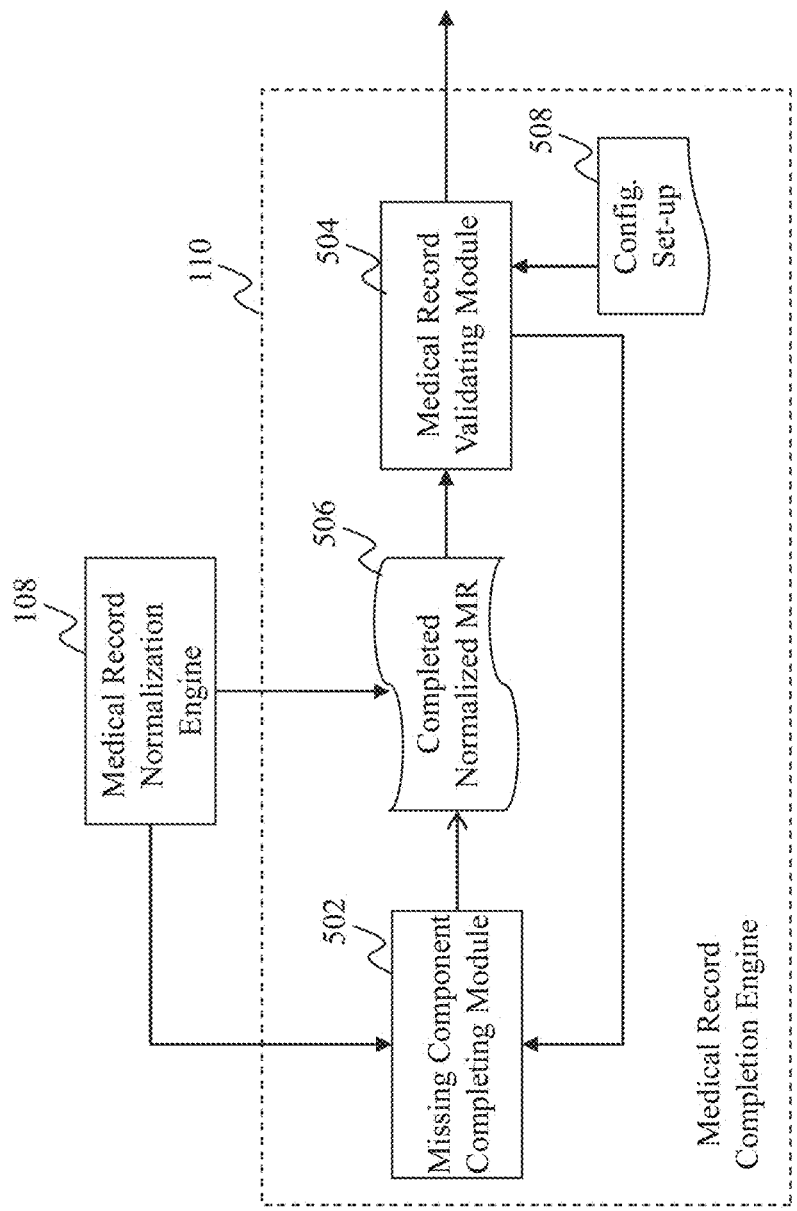
FIG. 5 illustrates an exemplary diagram of a medical record completion engine, according to an embodiment of the present teaching.

FIG. 5 illustrates an exemplary diagram of a medical record completion engine 110, according to an embodiment of the present teaching. The medical record completion engine 110 in this embodiment includes a missing component completing module 502 and a medical record validating module 504. If any missing component with an unpopulated value of a normalized medical record is identified by the medical record normalization engine 108, the missing component completing module 502 is responsible for estimating the value based on populated values of other components of the medical record in accordance with a model selected based on the type of missing component. As will be described later in detail, each type of the component may be associated with a particular model for completing the unpopulated value, e.g., an inference model based on a known mathematical relationship, patient information, or common medical knowledge, and a statistic model based on mining of historical, actual medical transaction data (e.g., prescription strings stored in the prescription string database 104). Once all missing components are filled with estimated values, a completed normalized medical record 506 is generated. In some embodiments, if values of all components of the medical record can be populated by the medical record normalization engine 108, then the completed normalized medical record 506 is generated without the missing component completing module 502.

The medical record validating module 504 in this embodiment is configured to validate the completed normalized medical record 506 to see if it is clinically correct. The medical record validating module 504 may determine the patient care setting of the received medical record by obtaining analytic influence information in multiple dimensions. Based on the same or similar patient care setting, the medical record validating module 504 retrieves clinically-proven qualified medical suggestions and compares values of the completed normalized medical record 506 with the retrieved medical suggestions to see if there are any discrepancies therebetween. In some embodiments, a configuration set-up 508 may be applied to the medical record validating module 504 for various configurations. For example, a threshold may be set to determine whether the discrepancy has reached a level that a flag needs to be raised. The configuration set-up 508 may also set whether values of all components are to be validated or just the estimated unpopulated values of the missing components are to be validated.

Figure 6:
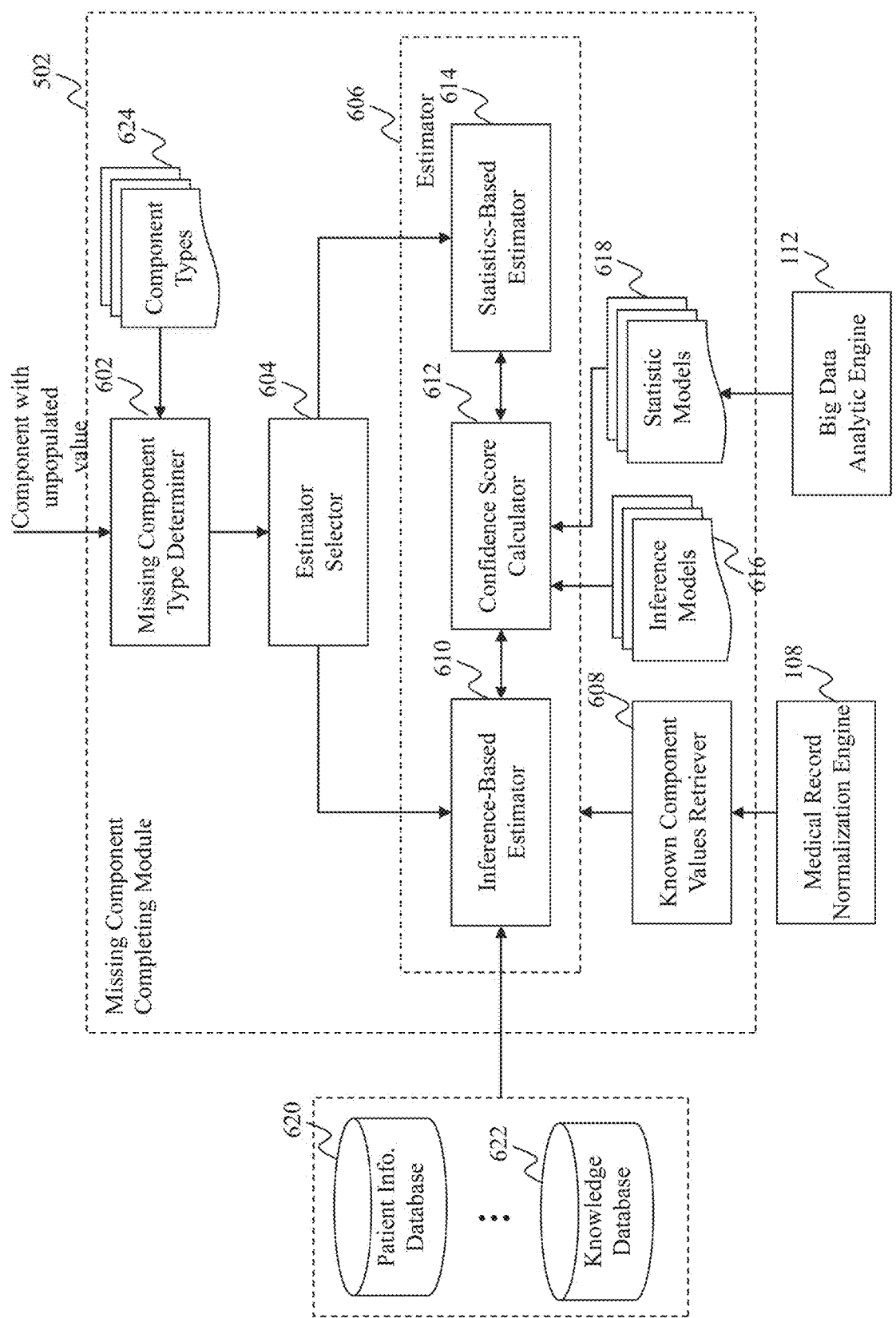
FIG. 6 illustrates an exemplary diagram of a missing component completing module, according to an embodiment of the present teaching.

FIG. 6 illustrates an exemplary diagram of a missing component completing module 502, according to an embodiment of the present teaching. In this embodiment, the missing component completing module 502 includes a missing component type determiner 602, an estimator selector 604, estimators 606, and known component values retriever 608. The missing component type determiner 602 determines the type of each missing component based on the standard component types 624. Based on the type of each missing component, the estimator selector 604 determines the appropriate estimators 606 to be used to estimate the unpopulated value. In this embodiment, the estimators 606 includes an inference-based estimator 610, a confidence score calculator 612, and a statistics-based estimator 614.

Inference models 616 may be used by the inference-based estimator 610 in conjunction with the confidence score calculator 612 to estimate an unpopulated value. In some embodiments, the inference may be made based on information stored in the patient information database 620 and/or the knowledge database 622. For example, if it is known that the drug ID of the medical record is for a Tylenol tablet, and based on medical knowledge from the knowledge database 622 that a Tylenol tablet can only be taken by mouth, then the inference-based estimator 610 can estimate the unpopulated value of the "route" component as "oral" with a relatively high confidence score. In another example, if it is known from the patient information database 620 that the patient is an infant, and it is known from the knowledge database 622 that the dose of Tylenol is 40 mg for an infant 6-11 pounds and is 80 mg for an infant 12-17 pounds, then the inference-based estimator 610 can estimate the unpopulated value of the "dose" component as "40 mg" with a confidence score of "50%" or "80 mg" with a confidence score of "50%."

In some embodiments, the inference may be made via a mathematical relationship based on populated values of other components in the medical record retrieved by the known component values retriever 608 from the medical record normalization engine 108. For example, if the value of the "frequency" component is not populated from the original medical record, while the values of the "duration" and "dispense quantity" components are populated, then the value of the "frequency" component may be calculated by the mathematical relationship of "frequency=dispense quantity/duration." In some cases, unrounded numbers may be obtained based on the calculation, and they may be rounded up or rejected as errors based on confidence scores calculated by the confidence score calculator 612.

The statistic models 618 are generated by the big data analytic engine 112 by mining the historical, actual medical transaction data of the general population of patients. As described in detail above, for medication prescription type of medical records, popular prescription strings may be mined and ranked in the prescription string database 104 by the statistic models 618 as shown in FIG. 15. Based on the populated values of other components of the medical record, e.g., the drug ID, the top ranked prescription strings with the same populated values of the same components are retrieved by the statistics-based estimator 614. The statistics-based estimator 614 then estimates the likely values of the missing component by looking up the values of the same component in the retrieved top prescription strings. Each estimated value may be associated with a confidence score calculated by the confidence score calculator 612. For example, if the value of the "route" component is missing for an antibiotic medication prescription, then the statistics-based estimator 614 may retrieve the top ranked prescription strings with the same drug ID to check the route of administration in those prescription strings. If the route is "oral" in most of the prescription strings and is "intra-muscular" in a few of the prescription strings, then the statistics-based estimator 614 may estimate the unpopulated value of the "route" component as "oral" with a high confidence score and "intra-muscular" with a low confidence score. It is understood that in some embodiments, the inference models 616 and the statistic models 618 may be used together to estimate the same missing component. In the example above, if it is commonly known that the patient's age is not suitable for intra-muscular administration of that antibiotic, then the estimated value of "intra-muscular" may be rejected.

Figure 7:
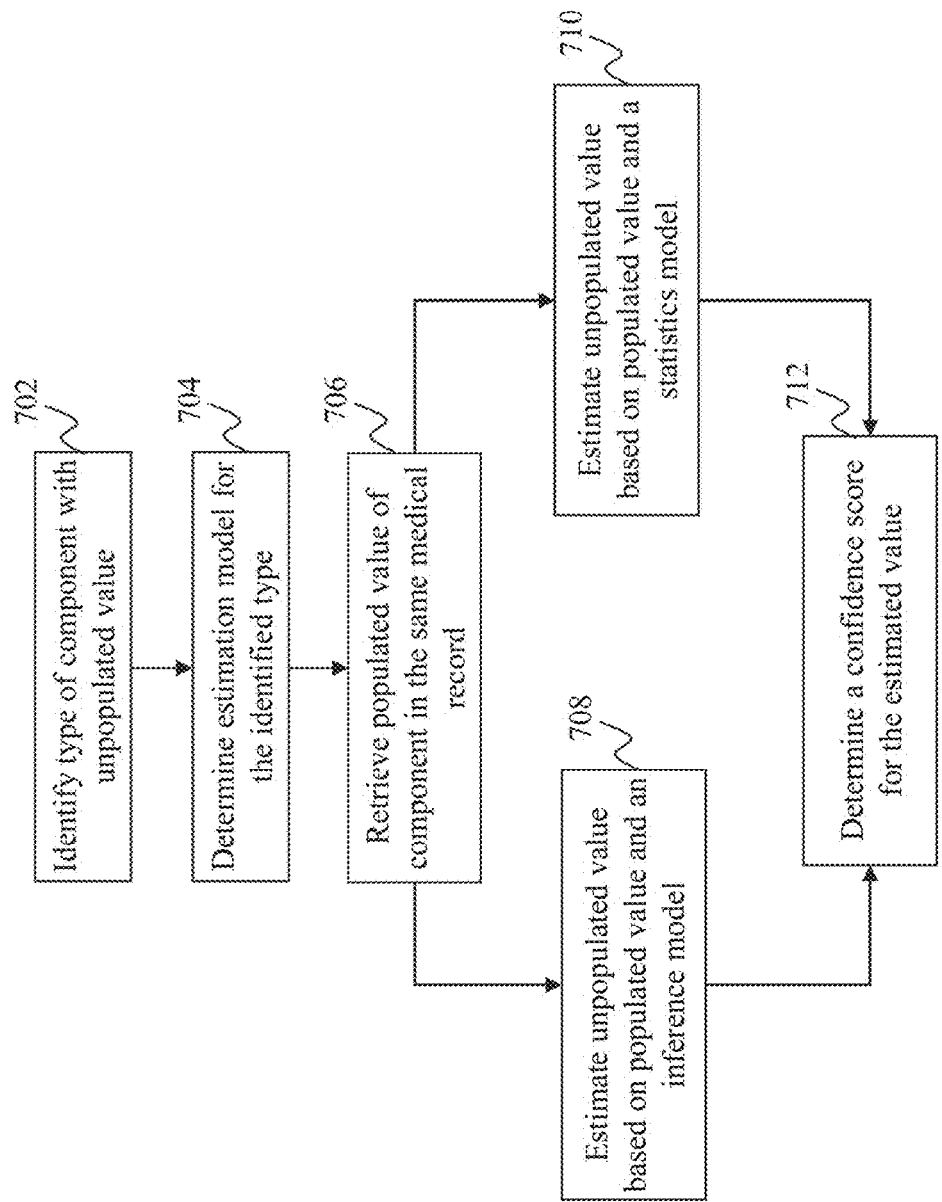
FIG. 7 is a flowchart of an exemplary process performed by the missing component completing module, according to an embodiment of the present teaching.

FIG. 7 is a flowchart of an exemplary process performed by the missing component completing module 502, according to an embodiment of the present teaching. Starting at 702, the type of a component with an unpopulated value (missing component) is identified. For example, for a medication prescription, the types of the component may include drug ID, action, dose, unit, route, timing, duration, frequency, dispense, dispense quantity, to name a few. At 704, based on the identified type of the missing component, the estimation model is determined. The estimation model includes, for example, an inference model and a statistics model. At 706, one or more populated values of components in the same medical record are retrieved. For example, the drug ID may be retrieved for a medication prescription. If the inference model is determined to be used for estimating an unpopulated value, at 708 the unpopulated value is estimated based on the retrieved one or more populated values and the inference model. In one example, the unpopulated value may be mathematically calculated based on the one or more populated values. In another example, the unpopulated value may be inferred based on common medical knowledge and/or the patient's information. If the statistics model is determined to be used for estimating an unpopulated value, at 710 the unpopulated value is estimated based on the retrieved one or more populated values and the statistics model. For example, for a medication prescription, the unpopulated value may be estimated based on the most frequently prescribed medication strings with the same drug ID mined from the historical data. At 712, a confidence score is determined for the estimated value.

Figure 8:
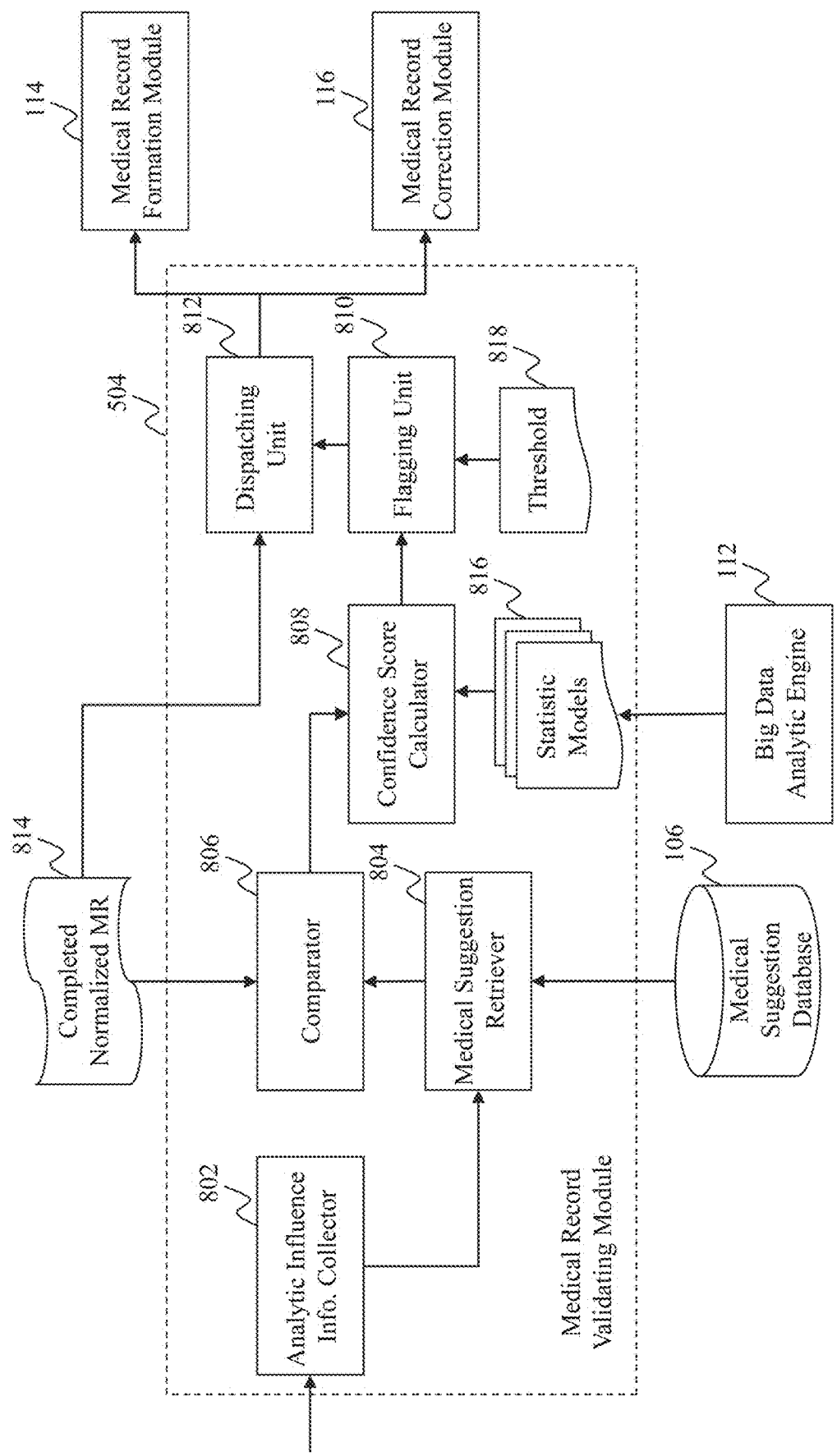
FIG. 8 illustrates an exemplary diagram of a medical record validating module, according to an embodiment of the present teaching.

FIG. 8 illustrates an exemplary diagram of a medical record validating module 504, according to an embodiment of the present teaching. The medical record validating module 504 in this embodiment includes an analytic influence information collector 802, a medical suggestion retriever 804, a comparator 806, a confidence score calculator 808, a flagging unit 810, and a dispatching unit 812. The analytic influence information collector 802 is configured to collect analytic influence information in multiple dimensions that is helpful in determining the patient care setting associated with the received medical record and/or the patient. Based on the patient care setting, the medical suggestion retriever 804 retrieves the top ranked medical suggestions in the same or similar patient care setting. The retrieved medical suggestions are then used by the comparator 806 to be checked against the completed normalized medical record 814 to find any discrepancies between the corresponding values in the same component. As mentioned above, the medical suggestions are mined and ranked in the medical suggestion database 106 based on statistics models 816, which may be used by the confidence score calculator 808 in determining the confidence score for each validation. The confidence score is then provided to the flagging unit 810 to be compared with a threshold 818 to determine whether the discrepancy should raise a flag. If the discrepancy is significant compared with the threshold 818, then the dispatching unit 812 forwards the completed medical record 814 to the medical record correction engine 116. If there is no discrepancy or the discrepancy is insignificant compared with the threshold 818, then the dispatching unit 812 forwards the completed medical record 814 to the medical record formation engine 114.

For example, if it is known that the medical record is a Tylenol prescription prescribed by a pediatrician and/or that the patient is an infant diagnosed with the common cold, then the top ranked medication prescriptions in the same patient care setting (infant with the common cold or prescribed by a pediatrician) are retrieved. If the comparator 806 finds that the dose in the completed medical record 814 is four times higher than the highest dose in the retrieved medication prescriptions, and the confidence score calculator 808 calculates that the large discrepancy causes a low confidence score for the dose value in the medical record. Then a flag may be raised to the dose value of the Tylenol prescription, and the Tylenol prescription is sent to the medical record correction engine 116. If the comparator 806 finds that all values in the Tylenol prescription are within the corresponding value range in the retrieved medication prescriptions, then the Tylenol prescription passes the validation process with a high confidence score.

Figure 9:
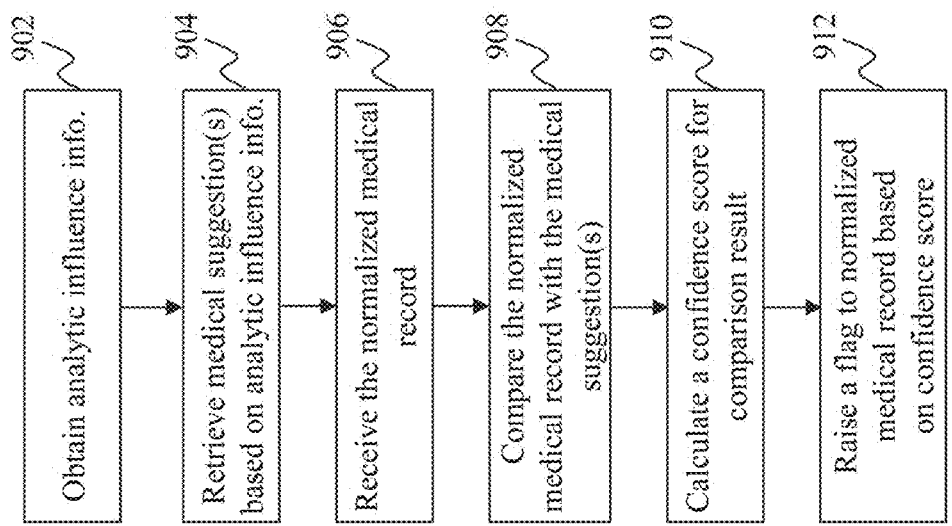
FIG. 9 is a flowchart of an exemplary process performed by medical record validating module, according to an embodiment of the present teaching.

FIG. 9 is a flowchart of an exemplary process performed by medical record validating module 504, according to an embodiment of the present teaching. Starting at 902, analytic influence information is obtained. The analytic influence information may be associated with the medical record and/or the patient and is in multiple dimensions. The dimensions include, for example, doctor specialties, disease diagnosis, symptoms, and patient profile. At 904, medical suggestions may be retrieved based on the obtained analytic influence information. The medical suggestions may be mined from historical medical transaction data and are organized in a ranked manner with respect to the dimensions of the analytic influence information. Based on the available analytic influence information, the top ranked medical suggestions are retrieved. These qualified medical suggestions may be considered as clinically correct as they are top ranked medical records mined from actual medical transaction data. The normalized medical record is received at 906. At 908, the values of the normalized medical record are compared with the corresponding values of the retrieved medical suggestions. At 910, a confidence score is calculated for the comparison result. At 912, based on the confidence score, a flag may be raised with respect to a value of the normalized medical record indicating that the value may not be clinically correct.

Figure 10:
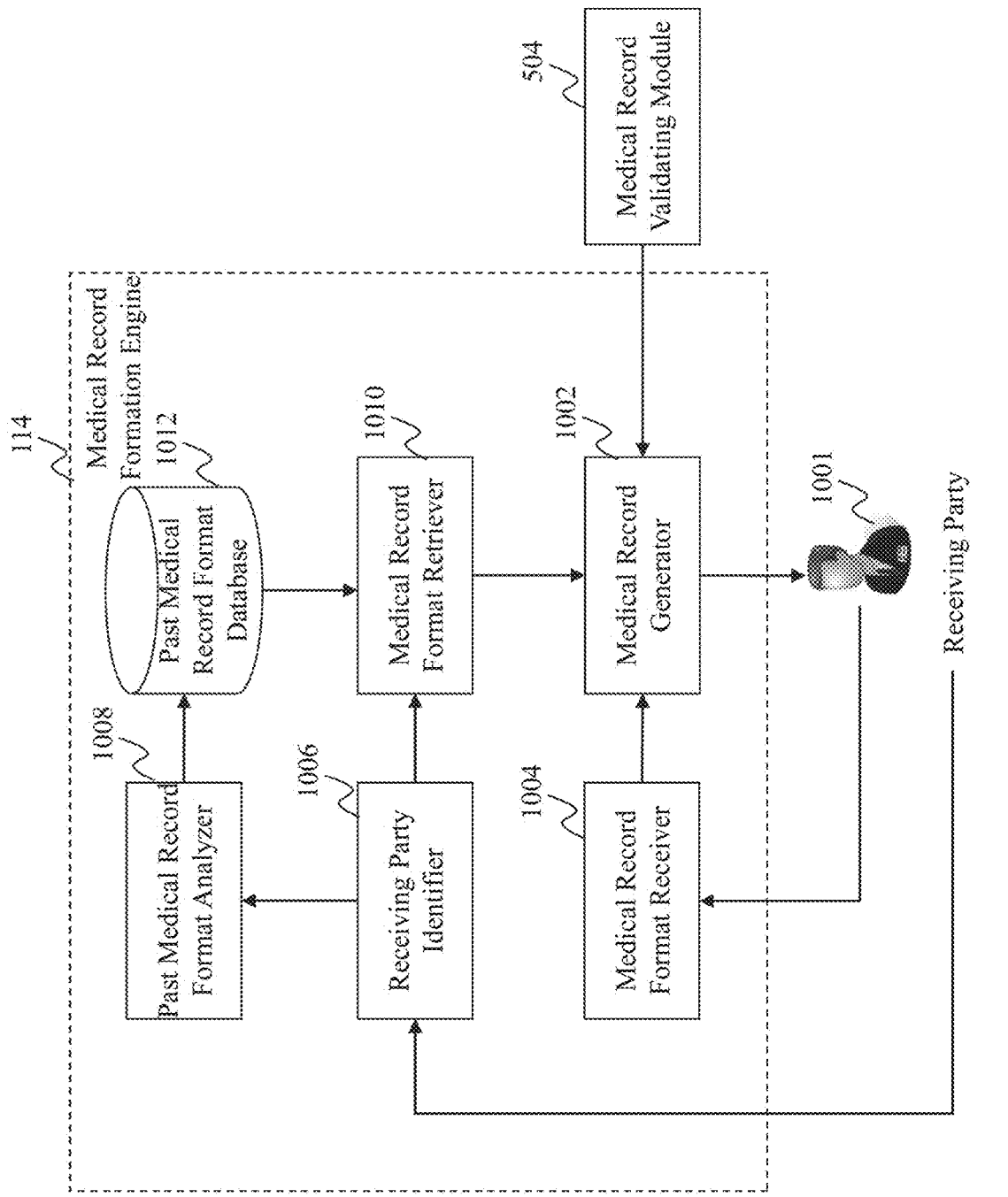
FIG. 10 illustrates an exemplary diagram of a medical record formation engine, according to an embodiment of the present teaching.

FIG. 10 illustrates an exemplary diagram of a medical record formation engine 114, according to an embodiment of the present teaching. The medical record formation engine 114 in this embodiment includes a medical record generator 1002, a medical record format receiver 1004, a receiving party identifier 1006, a past medical record format analyzer 1008, and a medical record format retriever 1010. As each receiving party 1001 may have its own specification of format for receiving a medical record, a medical record format receiver 1004 tries to obtain an explicit instruction from the receiving party 1001 as to its preferred format. If such format cannot be obtained from the receiving party 1001 directly for any reason, the receiving party identifier 1006 identifies the identity of the receiving party 1001 and passes such information to the past medical record format analyzer 1008. The past medical record format analyzer 1008 then retrieves all medical records that have been sent by the receiving party 1001 from the past medical record format database 1012. The past medical record format analyzer 1008 then determines from those retrieved medical records that the specific format the receiving party 1001 prefers using. The medical record format retriever 1010 then retrieves such format and provides it to the medical record generator 1002. The medical record generator 1002 generates the new completed medical record by putting the validated values (including both the populated and estimated unpopulated values) together according to the format preferred by the receiving party 1001. The new completed medical record is then sent to the receiving party 1001.

Figure 11:
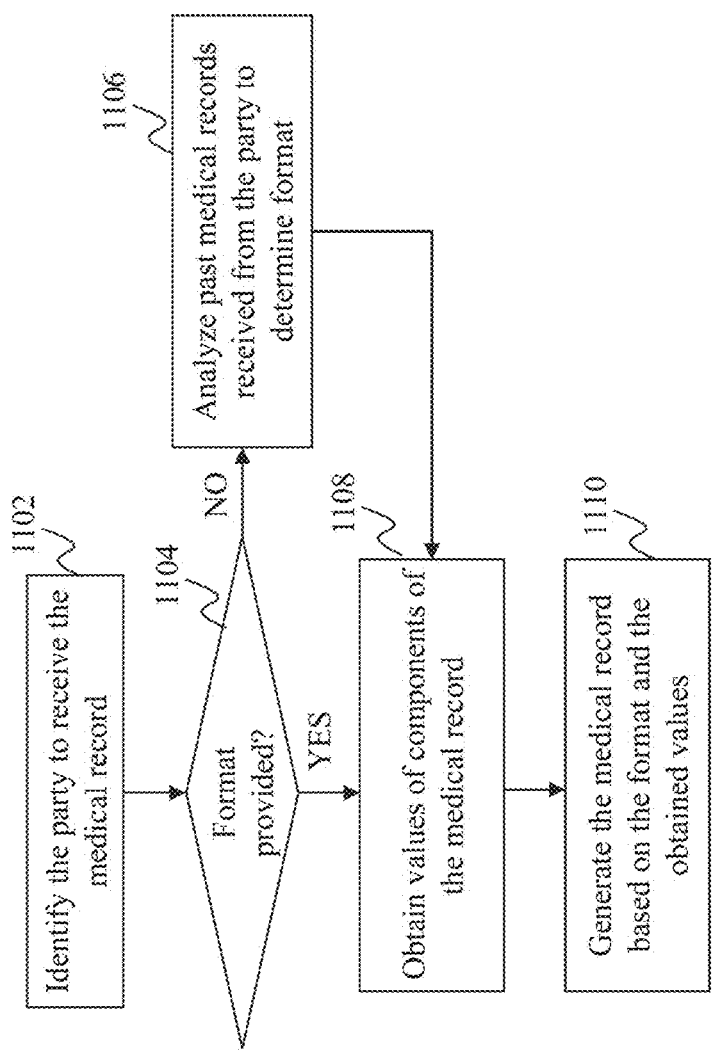
FIG. 11 is a flowchart of an exemplary process performed by the medical record formation engine, according to an embodiment of the present teaching.

FIG. 11 is a flowchart of an exemplary process performed by the medical record formation engine 114, according to an embodiment of the present teaching. Starting at 1102, the party to receive the medical record is identified. At 1104, whether the party has provided a format in which the medical record is to be sent is checked. If the answer is negative, at 1106, the past medical records received from the party are analyzed to determine the format that the party prefers using. At 1108, values of components of the received medical record are obtained. The values may be populated directly from the medical record during normalization or may be estimated using an inference or statistic model as described above. The values may also be validated based on historical medical suggestions and corrected if an error is identified. Nevertheless, at 1110, a new completed medical record is generated for the party based on the party's preferred format (either explicitly provided or analyzed according to historical data) and the obtained values of the received medical record.

Figure 12:
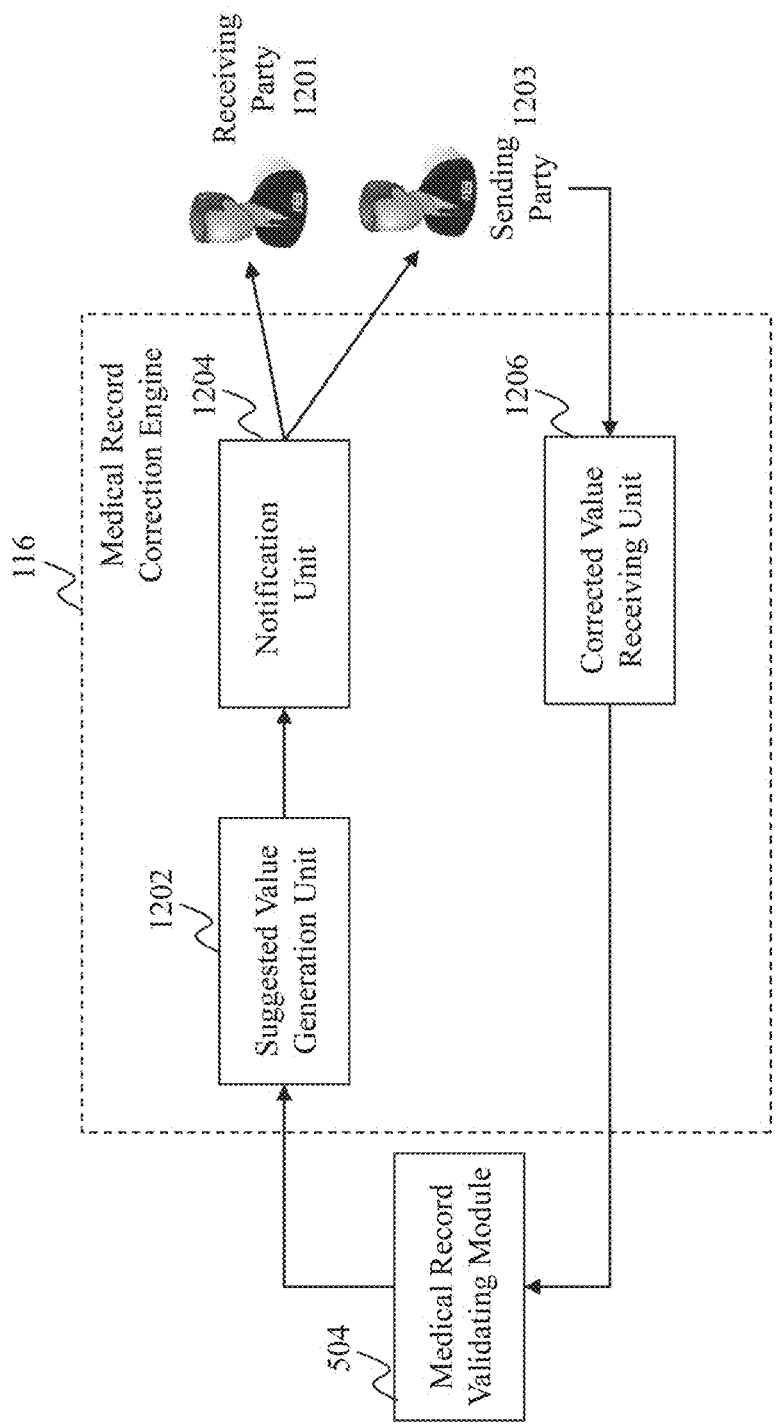
FIG. 12 illustrates an exemplary diagram of a medical record correction engine, according to an embodiment of the present teaching.

FIG. 12 illustrates an exemplary diagram of a medical record correction engine 116, according to an embodiment of the present teaching. The medical record correction engine 116 in this embodiment includes a suggested value generation unit 1202, a notification unit 1204, and a corrected value receiving unit 1206. For each value with a flag (e.g., failing to pass the validation process), the suggested value generation unit 1202 may provide one or more suggested values based on the values in the retrieved medical suggestions which are considered as clinically proven. Each of the suggested values may be associated with a confidence score obtained from the medical suggestion database 106. The notification unit 1204 may send a notification to the receiving party 1201 to whom the medical record is sent. The notification may be sent together with the completed medical record or sent as a separate warning message. The notification may indicate the value with a flag and the suggested values with corresponding confidence scores. In some embodiments, in addition to notifying the receiving party 1201, the notification unit 1204 may send a notification to the sending party 1203 from whom the medical record is received. The notification may indicate the value with a flag and the suggested values with corresponding confidence scores. If the sending party 1203, in response to the notification, sends an updated medical record with a corrected value, then the corrected value receiving unit 1206 passes the updated medical record to the medical record validating module 504 for re-validation.

Figure 13:
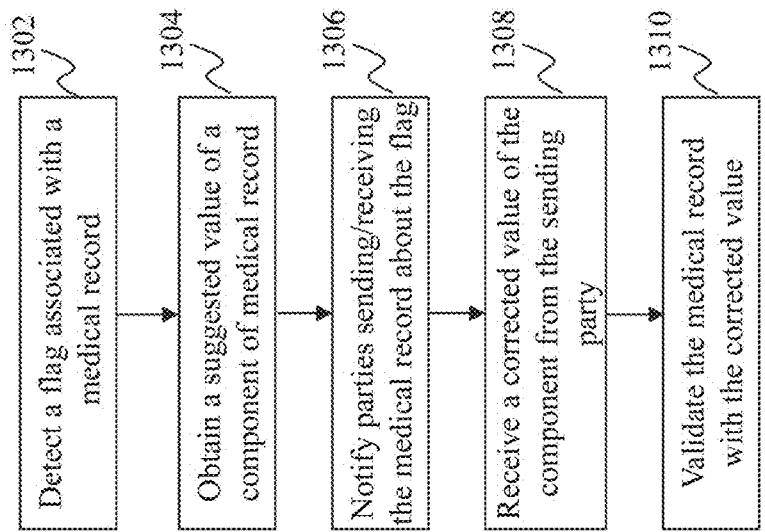
FIG. 13 is a flowchart of an exemplary process performed by the medical record correction engine, according to an embodiment of the present teaching.

FIG. 13 is a flowchart of an exemplary process performed by the medical record correction engine 116, according to an embodiment of the present teaching. Starting at 1302, a flag associated with a medical record is detected. The flag may be associated with a specific value of a component of the medical record. At 1304, a suggested value of the component may be obtained. The suggested value may be determined based on historical medical suggestions that have been considered as clinically correct. At 1306, the party receiving the medical record and/or the party sending the medical record are notified with the flag. The notification may also include the suggested value to replace the current value with the flag. At 1308, a corrected value of the component is received from the party sending the medical record. At 1310, the medical record with the corrected value is re-validated.

Figure 17:
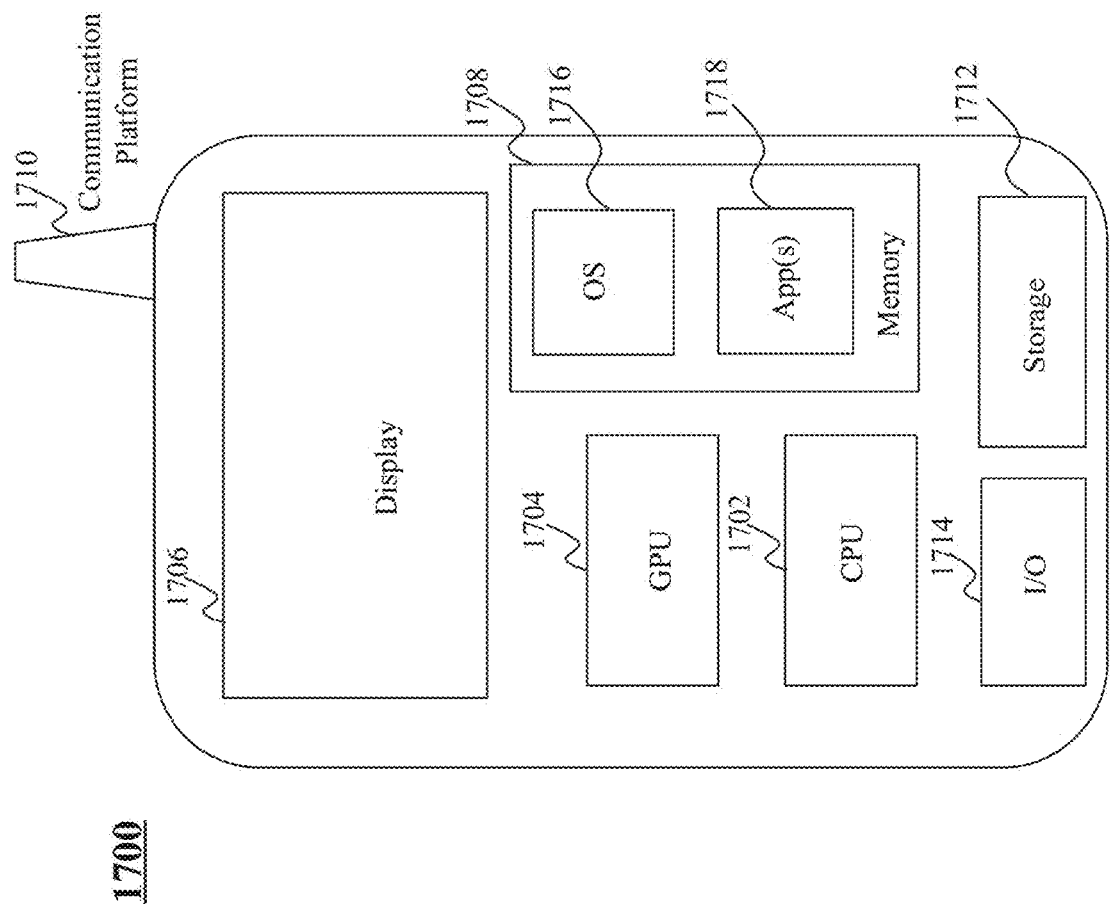
FIG. 17 depicts the architecture of a mobile device which can be used to implement a specialized system incorporating the present teaching.

FIG. 17 depicts the architecture of a mobile device which can be used to realize a specialized system implementing the present teaching. In this example, a device of the user 102 used for sending and receiving medical records may be a mobile device 1700, including, but is not limited to, a smart phone, a tablet, a music player, a handheld gaming console, a global positioning system (GPS) receiver, and a wearable computing device (e.g., eyeglasses, wrist watch, etc.), or in any other form. The mobile device 1700 in this example includes one or more central processing units (CPUs) 1702, one or more graphic processing units (GPUs) 1704, a display 1706, a memory 1708, a communication platform 1710, such as a wireless communication module, storage 1712, and one or more input/output (I/O) devices 1714. Any other suitable component, such as but not limited to a system bus or a controller (not shown), may also be included in the mobile device 1700. As shown in FIG. 17, a mobile operating system 1716, e.g., iOS, Android, Windows Phone, etc., and one or more applications 1718 may be loaded into the memory 1708 from the storage 1712 in order to be executed by the CPU 1702. The applications 1718 may include a web browser or any other suitable mobile apps used for health care related applications. Execution of the applications 1718 may cause the mobile device 1700 to perform some processing as being described in the present teaching. For example, user inputs may be received via the I/O devices 1714 and sent to the intelligent medical record completion system 100 via the communication platform 1710. Presentation of the completed medical records to the user may be made by the GPU 1704 in conjunction with the display 1706.

To implement the present teaching, computer hardware platforms may be used as the hardware platform(s) for one or more of the elements described herein. The hardware elements, operating systems, and programming languages of such computers are conventional in nature, and it is presumed that those skilled in the art are adequately familiar therewith to adapt those technologies to implement the processing essentially as described herein. A computer with user interface elements may be used to implement a personal computer (PC) or other type of work station or terminal device, although a computer may also act as a server if appropriately programmed. It is believed that those skilled in the art are familiar with the structure, programming, and general operation of such computer equipment and as a result the drawings should be self-explanatory.

Figure 18:
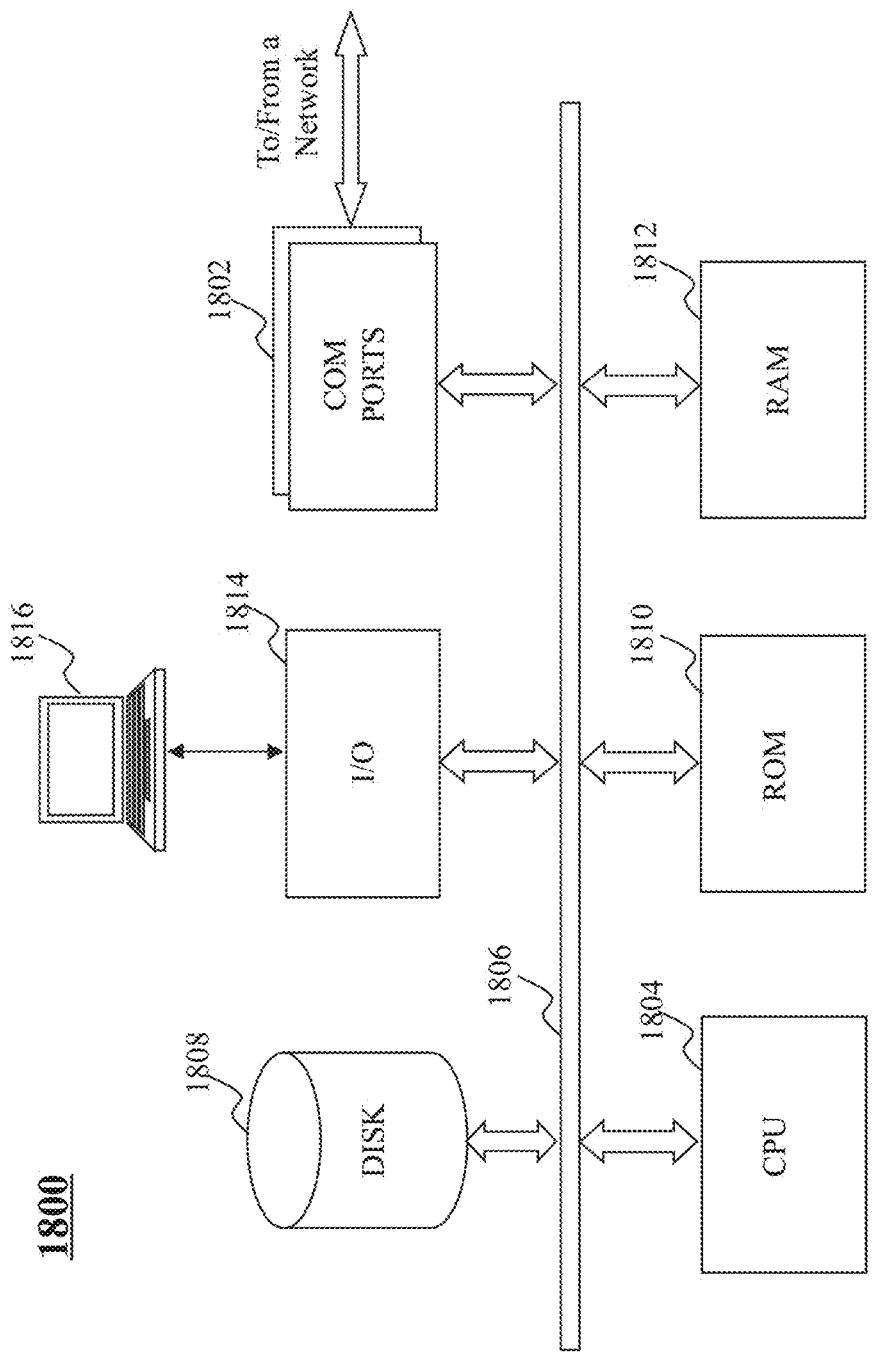
FIG. 18 depicts the architecture of a computer which can be used to implement a specialized system incorporating the present teaching.

FIG. 18 depicts the architecture of a computing device which can be used to realize a specialized system implementing the present teaching. The computer may be a general-purpose computer or a special purpose computer. This computer 1800 can be used to implement any components of the medical record completion architecture as described herein. Different components of the system, e.g., as depicted in FIG. 1, can all be implemented on one or more computers such as computer 1800, via its hardware, software program, firmware, or a combination thereof. Although only one such computer is shown, for convenience, the computer functions relating to medical record completion may be implemented in a distributed fashion on a number of similar platforms, to distribute the processing load.

The computer 1800, for example, includes COM ports 1802 connected to and from a network connected thereto to facilitate data communications. The computer 1800 also includes a CPU 1804, in the form of one or more processors, for executing program instructions. The exemplary computer platform includes an internal communication bus 1806, program storage and data storage of different forms, e.g., disk 1808, read only memory (ROM) 1810, or random access memory (RAM) 1812, for various data files to be processed and/or communicated by the computer, as well as possibly program instructions to be executed by the CPU 1804. The computer 1800 also includes an I/O component 1814, supporting input/output flows between the computer and other components therein such as user interface elements 1816. The computer 1800 may also receive programming and data via network communications.

Hence, aspects of the method of medical record completion, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

Those skilled in the art will recognize that the present teachings are amenable to a variety of modifications and/or enhancements. For example, although the implementation of various components described above may be embodied in a hardware device, it can also be implemented as a software only solution—e.g., an installation on an existing server. In addition, the medical record completion system and its components as disclosed herein can be implemented as a firmware, firmware/software combination, firmware/hardware combination, or a hardware/firmware/software combination.

While the foregoing has described what are considered to constitute the present teachings and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

I claim:

1. A method, implemented on at least one computing device each of which has at least one processor, storage, and a communication platform connected to a network for completing a medical record, the method comprising:

tracking medical transaction data in a large general population of patients to generate a data map, the data map pairing each of a plurality of medical suggestions with one or more analytic influence dimensions, each medical suggestion representing a medical transaction recommended by a medical professional and each analytic influence dimension in the data map specifying an attribute of a patient or an attribute of a physician associated with the medical transaction data, and each dimension-medical suggestion pair in the data map having a respective confidence score indicative of a degree of match between the medical suggestion and the analytic influence dimension over the large general population of patients, wherein tracking the medical transaction data includes dynamically updating the data map via analysis of new medical transaction data from the large general population of patients;

receiving a medical record of a patient, wherein the medical record is associated with a plurality of components comprising a first component with a populated value and a second component with an unpopulated value;

estimating a value for the second component based on the populated value of the first component in accordance with a first model wherein the first model is dynamically updated based on data related to the new medical transaction data for the large general population of patients;

identifying one or more analytic influence dimensions for the medical record, each of the one or more analytic influence dimensions specifying an attribute of the patient or an attribute of a physician associated with the medical record;

obtaining, from the data map, relevant dimension-medical suggestion pairs, the relevant dimension-medical suggestion pairs having an analytic influence dimension in the data map that matches one of the one or more analytic influence dimensions for the medical record;

selecting a plurality of highest-ranked relevant dimension-medical suggestion pairs based on the respective confidence scores from the data map;

determining whether a component with a discrepancy exists by comparing the value of each of the plurality of components with a value of a corresponding component from the plurality of highest-ranked relevant dimension-medical suggestion pairs to determine a discrepancy; and responsive to identifying a component with a discrepancy and to determining that the discrepancy satisfies a threshold:
receiving a corrected value for the component with the discrepancy, and
updating the medical record with the corrected value.

2. The method of claim 1, further comprising:
normalizing the medical record to generate a normalized medical record having the plurality of components comprising the first component with the populated value and the second component with the unpopulated value.

3. The method of claim 2, further comprising:
obtaining a medical record format associated with a user;
converting the normalized medical record into the medical record format; and
sending the converted normalized medical record to the user.

4. The method of claim 1, wherein the first model includes an inference model with rules for calculating the estimated value based on one or more values of populated components in the medical record.

5. The method of claim 1, wherein the first model includes a statistics model generated from the medical transaction data, the statistics model including, for each of a plurality of components in a medical record, a ranking representing a degree of match between the component and a normalized medical record.

6. The method of claim 1, wherein the degree of match between the medical suggestion and the analytic influence dimension in the data map is based on occurrences of the dimension-medical suggestion pairs in the tracked medical transaction data.

7. The method of claim 2, wherein the medical record is normalized based on a second model that is dynamically updated based on data related to medical transactions of the large general population of patients.

8. The method of claim 7, wherein the second model includes a mapping from a plurality of permutations to a term.

9. The method of claim 1, wherein an analytic influence dimension specifying an attribute of the patient includes at least one of:
disease diagnosis;
symptoms; or
patient profile.

10. The method of claim 1, wherein the medical record is in a natural language.

11. A system for completing a medical record, comprising:
at least one processor; and
memory storing instructions that, when executed by the at least one processor, cause the system to:
generate and dynamically update a data map by analyzing medical transaction data in a large general population of patients, the data map pairing each of a plurality of medical suggestions from the medical transaction data with one or more analytic influence dimensions, each medical suggestion representing a medical transaction recommended by a medical professional and each analytic influence dimension in the data map specifying an attribute of a patient or an attribute of a physician associated with the medical transaction data, and each dimension-medical suggestion pair in the data map having a respective confidence score indicative of a degree of match between the medical suggestion and the analytic influence dimension over the large general population of patients, wherein dynamically updating the data map occurs via analysis of new medical transaction data for the large general population of patients,
receive a medical record of a patient, wherein the medical record is associated with a plurality of components comprising a first component with a populated value and a second component with an unpopulated value, and estimate a value for the second component based on the populated value of the first component in accordance with a first model wherein the first model is dynamically updated based on data related to the new medical transaction data for the large general population of patients,
identify one or more analytic influence dimensions for the medical record, each of the one or more analytic influence dimensions specifying an attribute of the patient or an attribute of a physician associated with the medical record,
obtain, from the data map, relevant dimension-medical suggestion pairs, the relevant dimension-medical suggestion pairs having an analytic influence dimension in the data map that matches one of the one or more analytic influence dimensions for the medical record,
select a plurality of highest-ranked relevant dimension-medical suggestion pairs based on the respective confidence scores in the data map,
determine whether a component with a discrepancy exists by comparing the value of each of the plurality of components with a value of a corresponding component from the plurality of highest-ranked relevant dimension-medical suggestion pairs to determine a discrepancy, and
responsive to identifying a component with a discrepancy and to determining that the discrepancy satisfies a threshold, receive a corrected value for the component with the discrepancy and update the medical record with the corrected value.

12. The system of claim 11, the instructions further causing the system to:
normalize the medical record to generate a normalized medical record having the plurality of components comprising the first component with the populated value and the second component with the unpopulated value.

13. The system of claim 12, the instructions further causing the system to:
obtain a medical record format associated with a user;
convert the normalized medical record into the medical record format; and
send the converted normalized medical record to the user.

14. The system of claim 11, wherein the first model includes an inference model with rules for calculating the estimated value based on one or more values of populated components in the medical record.

15. The system of claim 11, wherein the first model includes a plurality of medical records, each of which being associated with rankings with respect to the plurality of components.

16. The system of claim 11, wherein the degree of match between the medical suggestion and the analytic influence dimension in the data map is based on occurrences of the dimension-medical suggestion pairs in the analyzed medical transaction data.

17. The system of claim 12, wherein the medical record is normalized based on a second model that is dynamically updated based on data related to medical transactions of the large general population of patients.

18. The system of claim 17, wherein the second model includes a mapping from a plurality of permutations to a term.

19. The system of claim 11, wherein an analytic influence dimension specifying an attribute of the patient includes at least one of:
   disease diagnosis;
   symptoms; or
   patient profile.

20. A non-transitory machine readable medium having information recorded thereon for completing a medical record, wherein the information, when read by a machine, causes the machine to perform the steps of:
   analyzing medical transaction data in a large general population of patients to generate and dynamically update a data map, the data map pairing each of a plurality of medical suggestions with one or more analytic influence dimensions, each medical suggestion representing a medical transaction recommended by a medical professional and each analytic influence dimension in the data map specifying an attribute of a patient or an attribute of a physician associated with the medical transaction data, and each dimension-medical suggestion pair in the data map having a respective confidence score indicative of a degree of match between the medical suggestion and the analytic influence dimension in the medical transaction data over the large general population of patients, wherein dynamically updating the data map occurs via analysis of new medical transaction data for the large general population of patients;
   receiving a medical record of a patient, wherein the medical record is associated with a plurality of components comprising a first component with a populated value and a second component with an unpopulated value;
   estimating a value for the second component based on the populated value of the first component in accordance with a first model, wherein the first model is dynamically updated based on data related to the new medical transaction data for the large general population of patients;
   identifying one or more analytic influence dimensions for the medical record, each of the one or more analytic influence dimensions specifying an attribute of the patient or an attribute of a physician associated with the medical record;
   obtaining, from the data map, relevant dimension-medical suggestion pairs, the relevant dimension-medical suggestion pairs having an analytic influence dimension in the data map that matches one of the one or more analytic influence dimensions for the medical record;
   selecting a plurality of highest-ranked relevant dimension-medical suggestion pairs based on the respective confidence scores in the data map;
   determining whether a component with a discrepancy exists by comparing the value of each of the plurality of components with a value of a corresponding component from the plurality of highest-ranked relevant dimension-medical suggestion pairs to determine a discrepancy; and
   responsive to identifying a component with a discrepancy and to determining that the discrepancy satisfies a threshold:
      receiving a corrected value for the component with the discrepancy, and
      updating the medical record with the corrected value.

21. The method of claim 1, wherein the medical transactions recommended by a medical professional include at least one of a medication drug prescription, a physical therapy referral, a diet recommendation, or a medical test.

* * * * *